United States Patent
Cecchi et al.

(10) Patent No.: US 10,207,111 B2
(45) Date of Patent: *Feb. 19, 2019

(54) ANALYZER FOR BEHAVIORAL ANALYSIS AND PARAMETERIZATION OF NEURAL STIMULATION

(71) Applicant: International Business Machines Corporation, Armonk, NY (US)

(72) Inventors: Guillermo A. Cecchi, New York, NY (US); James R. Kozloski, New Fairfield, CT (US); Clifford A. Pickover, Yorktown Heights, NY (US); Irina Rish, Rye Brook, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 2 days.

This patent is subject to a terminal disclaimer.

(21) Appl. No.: 15/861,794

(22) Filed: Jan. 4, 2018

(65) Prior Publication Data

US 2018/0126167 A1    May 10, 2018

Related U.S. Application Data

(63) Continuation of application No. 14/637,519, filed on Mar. 4, 2015, now Pat. No. 9,943,689.

(51) Int. Cl.
*A61N 1/36* (2006.01)
*A61N 1/05* (2006.01)

(52) U.S. Cl.
CPC ....... *A61N 1/36132* (2013.01); *A61N 1/0534* (2013.01); *A61N 1/36139* (2013.01)

(58) Field of Classification Search
CPC ............ A61N 1/36139; A61N 1/37282; A61N 1/36067; A61N 1/36071; A61N 1/36082
USPC ........................................................ 607/45
See application file for complete search history.

(56) References Cited

U.S. PATENT DOCUMENTS

| | | | |
|---|---|---|---|
| 2005/0033378 A1* | 2/2005 | Sheffield | A61N 1/08 607/45 |
| 2010/0041000 A1* | 2/2010 | Glass | G09B 5/02 434/179 |
| 2014/0074180 A1* | 3/2014 | Heldman | A61B 5/1101 607/45 |
| 2016/0256690 A1 | 9/2016 | Cecchi et al. | |
| 2016/0256691 A1 | 9/2016 | Cecchi et al. | |

OTHER PUBLICATIONS

List of IBM Patents or Patent Applications Treated As Related; Date Filed: Jan. 4, 2018, 2 pages.

* cited by examiner

*Primary Examiner* — Carl H Layno
*Assistant Examiner* — Jon Eric C Morales
(74) *Attorney, Agent, or Firm* — Cantor Colburn LLP; Rahan Uddin

(57) ABSTRACT

Embodiments are directed to a computer implemented neural stimulation system having a first module configured to derive neural data from muscle contractions or movements of a subject. The system further includes a second module configured to derive a neural state assessment of the subject based at least in part on the neural data. The system further includes a third module configured to derive at least one neural stimulation parameter based at least in part on the neural state assessment. The system further includes a fourth module configured to deliver neural stimulations to the subject based at least in part on the at least one neural stimulation parameter.

17 Claims, 8 Drawing Sheets

$(0,1,0,0...)$      EQUATION A $sim(a,b) = \vec{W}_a \cdot \vec{W}_b$      EQUATION B $G = \{N, E, W\}$      EQUATION C $\vec{W} = \vec{W}_{syn} \oplus \vec{W}_{sem} \oplus \vec{W}_{ntxt}$      EQUATION D $G_{sk} = \{N, E\}$      EQUATION E $H = \sum_n E_{nm} \vec{W}_n \vec{W}_m$      EQUATION F $M = M(\vec{F}_{brain}, C_{brain})$      EQUATION G $C(sample) = M(\vec{F}_{sample})$      EQUATION H

ANALYZER FOR BEHAVIORAL ANALYSIS AND PARAMETERIZATION OF NEURAL STIMULATION

DOMESTIC PRIORITY

This application is a continuation of U.S. application Ser. No. 14/637,519, filed Mar. 4, 2015, is now U.S. Pat. No. 9,943,689 the contents of which are incorporated by reference herein in its entirety.

BACKGROUND

The present disclosure relates in general to systems and methodologies for controlling the therapeutic application of neural stimulation. More specifically, the present disclosure relates to systems and methodologies for analyzing the results of muscle contractions or movements in order to develop parameters for controlling the therapeutic application of neural stimulation to treat neurological disorders.

Different types of therapeutic stimulation may be applied to neurological systems to treat variety of neurological disorders. For example, therapeutic neural stimulation may be applied to the brain to treat a variety of brain related disorders. One example of a therapeutic neural stimulation system is known generally as deep brain stimulation (DBS). DBS is a neurosurgical procedure involving the implantation of a medical device called a brain pacemaker, which sends electrical impulses, through implanted electrodes, to specific parts of the brain (brain nucleus) for the treatment of movement and affective disorders. DBS in select brain regions has provided therapeutic benefits for otherwise-treatment-resistant movement and affective disorders such as Parkinson's disease, essential tremor, dystonia, chronic pain, major depression and obsessive-compulsive disorder (OCD).

A contemporary DBS system includes three components, namely an implanted pulse generator (IPG), a lead and an extension. The IPG is a battery-powered neurostimulator encased in a titanium housing. The IPG sends electrical pulses to the brain to interfere with neural activity at the target site. The lead is a coiled wire insulated in polyurethane with four platinum iridium electrodes and is placed in one or two different nuclei of the brain. The lead is connected to the IPG by the extension, which is an insulated wire that runs below the skin and extends from the head down the side of the neck and behind the ear to the IPG. The IPG is placed subcutaneously below the clavicle or, in some cases, the abdomen. DBS leads are placed in the brain according to the type of symptoms to be addressed. For example, to treat non-Parkinsonian essential tremor, the lead is typically placed in the ventrointermediate nucleus of the thalamus.

Instruments for direct electrical brain stimulation are currently available from several companies (e.g., Medtronics, Neuromed, Cochlear Corp., Advanced Bionics). An important step in applying neural stimulation is determining the appropriate neural stimulation parameters in order to optimize efficacy of stimuli to be ultimately used in treatment. If the stimulation is electrical signals, the stimulation parameters may be frequency, pulse duration, duty cycle, etcetera. The effectiveness of a neural stimulation treatment can depend on the effectiveness of the criteria for choosing the stimulation parameters of a neural stimulation procedure.

SUMMARY

Embodiments are directed to a computer implemented neural stimulation system having a first module configured to derive neural data from muscle contractions or movements of a subject. The system further includes a second module configured to derive a neural state assessment of the subject based at least in part on the neural data. The system further includes a third module configured to derive at least one neural stimulation parameter based at least in part on the neural state assessment. The system further includes a fourth module configured to deliver neural stimulations to the subject based at least in part on the at least one neural stimulation parameter.

Embodiments are directed to a computer implemented neural stimulation method. The method includes deriving, by a processor, neural data from muscle contractions or movements of a subject. The method further includes deriving, by the processor, a neural state assessment of the subject based at least in part on the neural data. The method further includes deriving, by the processor, at least one neural stimulation parameter based at least in part on the neural state assessment. The method further includes delivering neural stimulations to the subject based at least in part on the at least one neural stimulation parameter.

Embodiments are further directed to a computer program product for implementing a neural stimulation system. The computer program product includes a computer readable storage medium having program instructions embodied therewith, wherein the computer readable storage medium is not a transitory signal per se. The program instructions are readable by a processor circuit to cause the processor circuit to perform a method that includes deriving, by the processor, neural data from muscle contractions or movements of a subject. The method further includes deriving, by the processor, a neural state assessment of the subject based at least in part on the neural data. The method further includes deriving, by the processor, at least one neural stimulation parameter based at least in part on said neural state assessment. The method further includes delivering neural stimulations to the subject based at least in part on the at least one neural stimulation parameter.

Additional features and advantages are realized through techniques described herein. Other embodiments and aspects are described in detail herein. For a better understanding, refer to the description and to the drawings.

BRIEF DESCRIPTION OF THE DRAWINGS

The subject matter which is regarded as embodiments is particularly pointed out and distinctly claimed in the claims at the conclusion of the specification. The foregoing and other features and advantages of the embodiments are apparent from the following detailed description taken in conjunction with the accompanying drawings in which:

Figure 1:
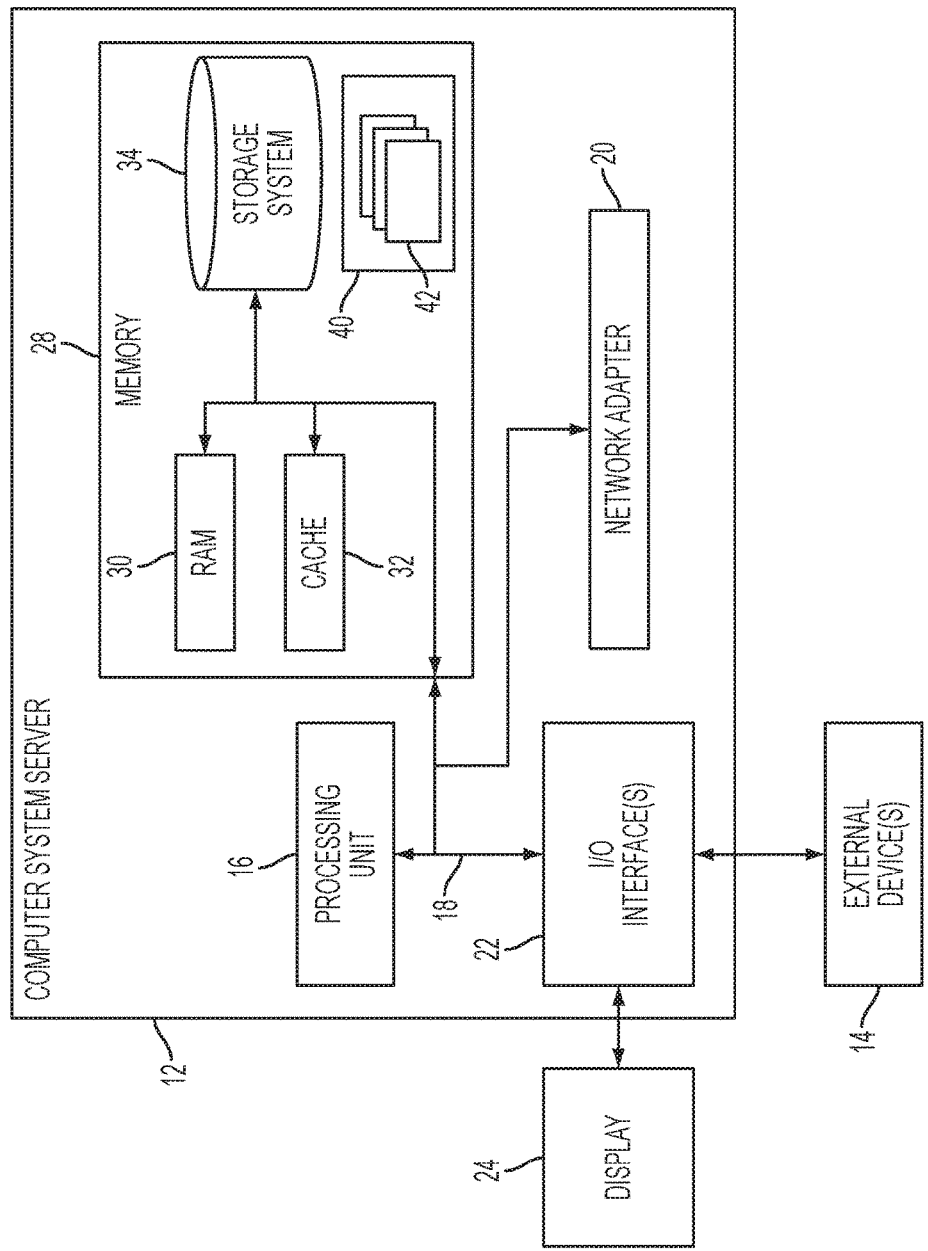
FIG. 1 depicts a cloud computing node according to one or more embodiments.

In the accompanying figures and following detailed description of the disclosed embodiments, the various elements illustrated in the figures are provided with three digit reference numbers. The leftmost digits of each reference number corresponds to the figure in which its element is first illustrated.

DETAILED DESCRIPTION

It is understood in advance that although this disclosure includes a detailed description on cloud computing, implementation of the teachings recited herein are not limited to a cloud computing environment. Rather, embodiments of the present disclosure are capable of being implemented in conjunction with any other type of computing environment now known or later developed. Additionally, although this disclosure includes a detailed description of analyzing text in order to derive parameters of a deep brain stimulation, implementation of the teachings recited herein are not limited to graphical text systems and deep brain stimulation systems. Rather, embodiments of the present disclosure are capable of being implemented in conjunction with any other type of system, now known or later developed, that analyzes any type of voluntary or involuntary muscle contractions or movements. Embodiments of the present disclosure are further capable of being implemented in conjunction with any other type of system, now known or later developed, that applies therapeutic neural stimulation to neurological systems.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows: Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 2:
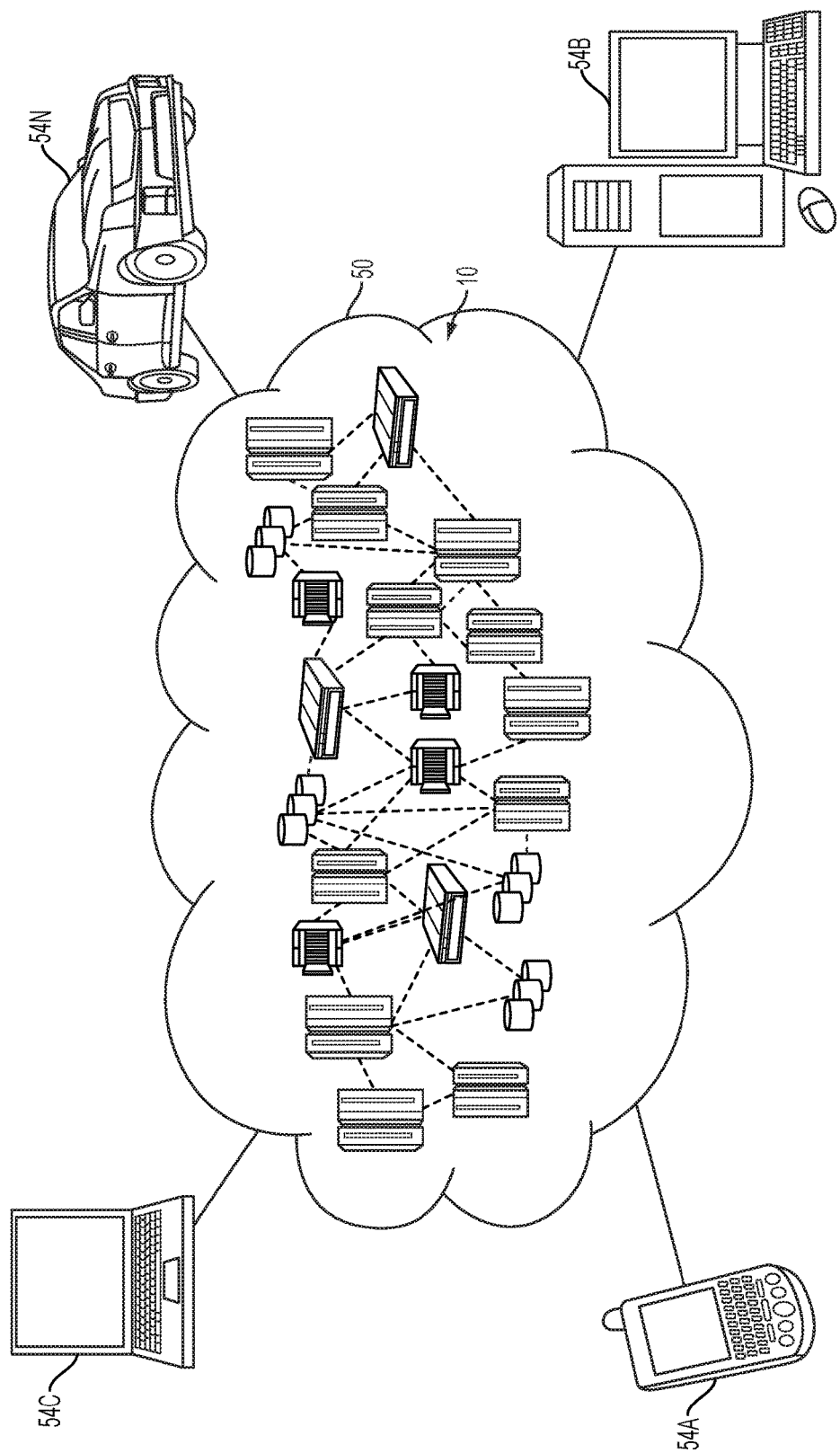
FIG. 2 depicts a cloud computing environment according to one or more embodiments.

Referring now to FIG. 2, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
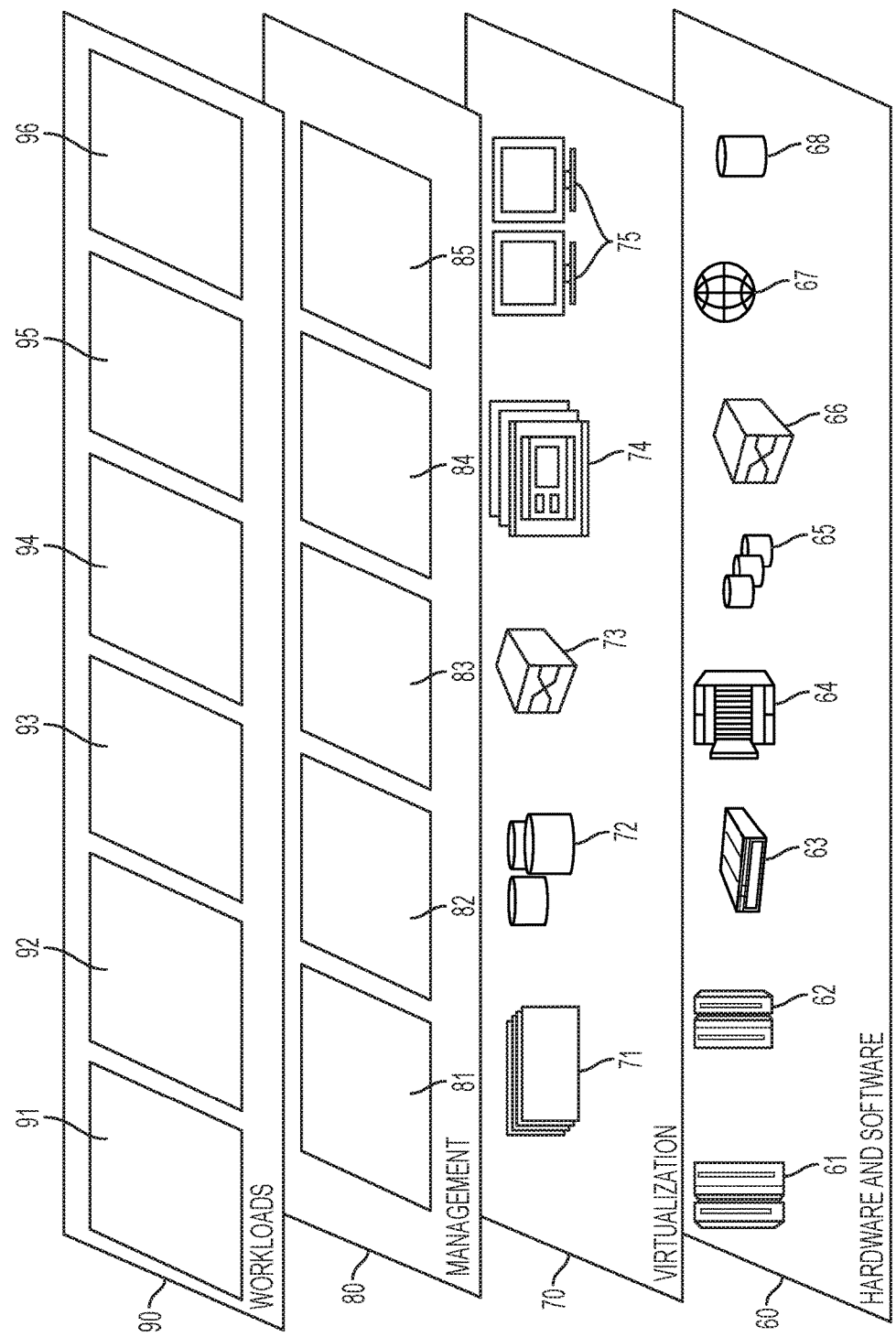
FIG. 3 depicts abstraction model layers according to one or more embodiments.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and a neural stimulation system support module 96 for developing parameters to control the therapeutic application of neural stimulation to treat neurological disorders.

The present disclosure relates in general to systems and methodologies for controlling the therapeutic application of neural stimulation. More specifically, the present disclosure relates to systems and methodologies for analyzing the results of muscle contractions or movements in order to develop parameters for controlling the therapeutic application of neural stimulation to treat neurological disorders. Workloads layer and neural stimulation system support module 96 may provide some or all of the functionality to support the one or more embodiments of the present disclosure.

As previously noted herein, different types of therapeutic stimulation may be applied to neurological systems to treat variety of neurological disorders. For example, therapeutic neural stimulation may be applied to the brain to treat a variety of brain related disorders. One example of a therapeutic neural stimulation system is known generally as DBS. DBS is a neurosurgical procedure involving the implantation of a medical device called a brain pacemaker, which sends electrical impulses, through implanted electrodes, to specific parts of the brain (brain nucleus) for the treatment of movement and affective disorders. DBS in select brain regions has provided therapeutic benefits for otherwise-treatment-resistant movement and affective disorders such as Parkinson's disease, essential tremor, dystonia, chronic pain, major depression and OCD.

An important step in applying neural stimulation is determining the appropriate neural stimulation parameters in order to optimize efficacy of stimuli to be ultimately used in treatment. If the stimulation is electrical signals, the stimulation parameters may be frequency, pulse duration, duty cycle, etcetera. The effectiveness of a neural stimulation treatment can depend on the effectiveness of the criteria for choosing the stimulation parameters of a neural stimulation procedure. Accordingly, achieving a natural classification of a given trajectory/graph of behavior and cognitive function is an optimal requirement for setting or modifying parameters and confidence levels for stimulation via neural stimulators such as DBS. Such a classification is often not available, or takes too long to determine for real-time intervention in neural processes such as brain activity.

The present disclosure provides a method for continuous graphical text analyzer calculations on an individual's speech, wherein such calculations produce categories and confidence levels which are input to a stimulus parameter set translation for neural stimulation (e.g., DBS). When a subject is near a transition into a state of psychiatric dysfunction (e.g., signs of impending delusions or schizophrenic thinking), the system of the present disclosure triggers neural stimulation having stimulation parameters selected to treat the state of psychiatric dysfunction. For example, where the neural stimulation is DBS, the system of the present disclosure triggers DBS in a particular set of output electrodes implanted in the brain. The graphical text analyzer utilized in connection with the present disclosure quantifies a trajectory or realization of a stochastic process, i.e., a sequence of states (e.g., multi-dimensional vectors) such as words in text.

In an exemplary embodiment according to the present disclosure, an individual undergoes DBS, and a system analyzes text-to-speech of the individual as a set of word or phrase vectors to categorize the individual's cognitive state. A preliminary category of the cognitive state is determined and used to predict the individual's cognitive trajectory and to update the individual's DBS. Additional data samples are extracted. The additional data samples may include written text, electroencephalogram (EEG) measurements, deep brain electrophysiology, behaviors in the world, etcetera, derived from a cloud computing environment, wearable devices on the individual, implanted DBS electrodes, and others. The additional data provide additional cognitive trajectories within a graph. The probability that a particular Markov chain produced a given trajectory is calculated. A Markov chain is a mathematical system that undergoes transitions from one state to another on a state space. It is a random process usually characterized as memoryless, i.e., the next state depends only on the current state and not on the sequence of events that preceded it. This specific kind of "memorylessness" is called the Markov property. Markov chains have many applications as statistical models of real-world processes. The DBS parameters used as one of the additional data samples, along with a second classification of the cognitive state, are used to determine if a change in the individual's cognitive state was clinically beneficial. The stimulation parameters are selected based at least in part on an identification of the simulations parameters that achieved behavior reclassifications/transition to another chain category and clinical outcome.

Figure 4:
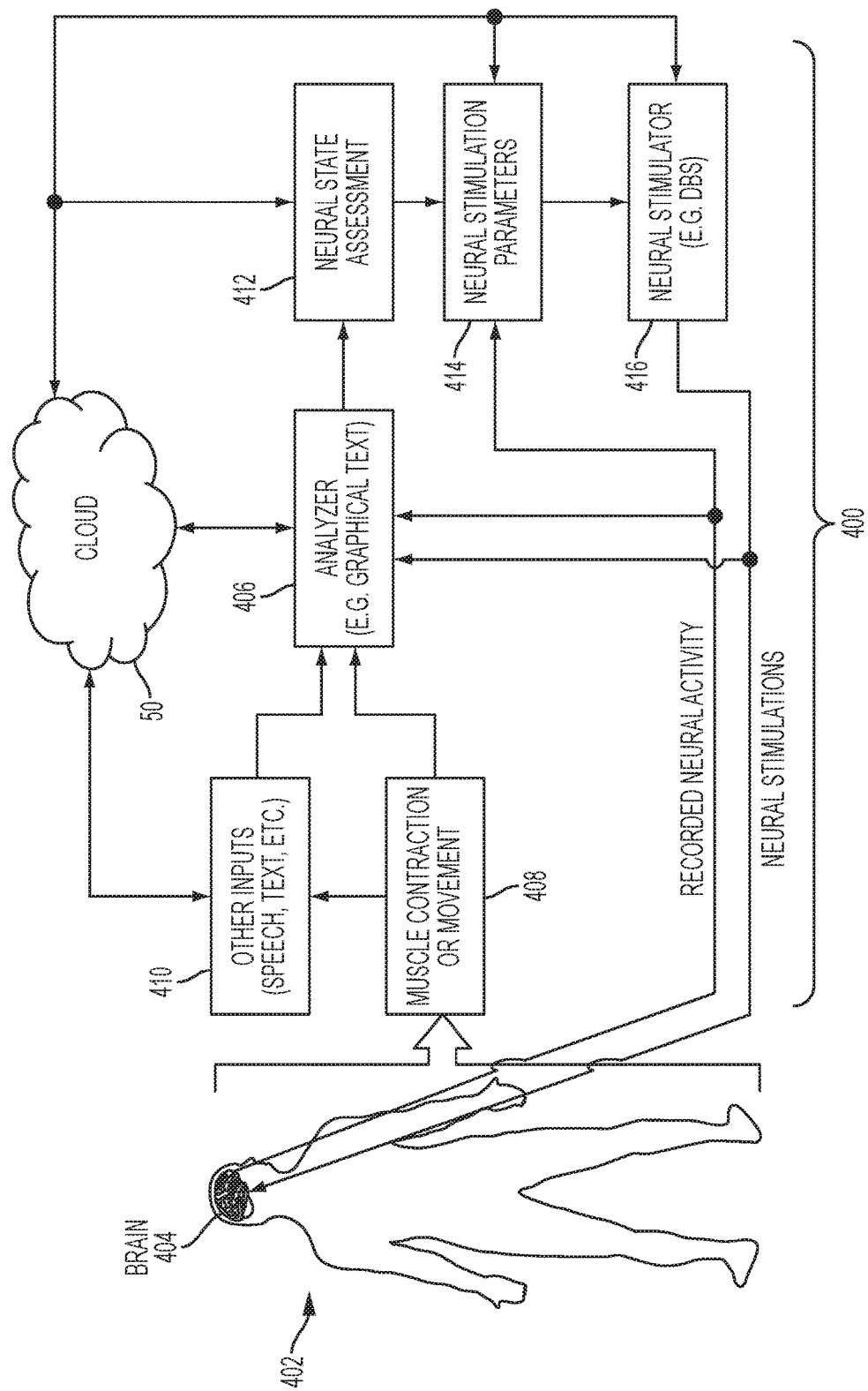
FIG. 4 depicts a diagram illustrating a neural stimulation system according to one or more embodiments.

Turning now to a more detailed description of the present disclosure, FIG. 4 depicts a diagram illustrating a neural stimulation system 400 interacting with a human 402 according to one or more embodiments. Neural stimulation system 400 includes an analyzer module 406, a muscle contractions or movements module 408, an other inputs module 410, cloud 50 (also shown in FIG. 2), a neural state assessment module 412, a neural stimulation parameters module 414 and a neural stimulator module 416, configured and arranged as shown. Cloud 50 may supplement, support or replace some or all of the functionality of muscle contractions or movements module 408, other inputs module 410, analyzer module 406, neural state assessment module 412, neural stimulation parameters module 414 and neural stimulator module 416. Additionally, some or all of the functionality of muscle contractions or movements module 408, other inputs module 410, analyzer module 406, neural state assessment module 412, neural stimulation parameters module 414 and neural stimulator module 416 may be implemented as a node 10 (shown in FIGS. 1 and 2) of cloud 50.

Neural stimulation system 400 determines the appropriate neural stimulation parameters (module 412) for applying neural stimulation to a neural system (e.g., brain 404) of human 402. Although brain 404 is shown in FIG. 4, it is understood that the present disclosure is applicable to stimulation applied to portions of the neural system of human 402 that extend beyond brain 404. Referring again to neural stimulation system 400, modules 408, 410 may work together or individually to provide inputs to analyzer module 406. More specifically, muscle contractions or movements module 408 senses the results of both voluntary and involuntary muscle contractions or movements by human 402, and other input module 410 optionally converts detected muscle contractions or movements into alternative formats. For example, where muscle contractions or movements detected by module 408 are the muscle contractions or movements that generate speech, other inputs module 410 may convert the detected speech to text. Other gestures created by muscle contractions or movements may also be reduced to tokens such as text descriptors, or nodes in a graph. In one or more embodiments, modules 408, 410 may also work together or individually to generate and/or detect voice, video or any other measurement that can be informative about a current neurological state (e.g., mental/emotional states) and changes to that neurological state (e.g., heart rate variability, blood pressure, galvanic skin conductance and EEG measurements, each of which may be collected using easy-to-use, inexpensive wearable devices). Module 408 may be implemented as any device that can detect and/or measure voluntary and/or involuntary muscle contractions or movements. Module 410 may be implemented as any device that can convert detected and/or measured voluntary and/or involuntary muscle contractions or movements to another format, such as a conversion of speech to text.

Analyzer module 406 extracts features of the various text, voice, video and other physiological measurements it receives. Each type of measurements may be used to generate a distinct set of features (e.g., voice pitch, facial expression features, heart rate variability as an indicator of stress level, etc.). In addition, features may be extracted from a derived data set of predictions about neural systems, e.g., their morphology and neurophysiological properties, including neurodynamical properties and neural connectivity. This derived data, inferred from measures of behavior and their related features, is herein referred to as neural data. The extracted features are fed to neural state assessment module 412 to determine a current or expected neural state (e.g., a predicted Parkinson's or OCD episode) of human 402 that corresponds to the extracted features. Neural stimulation parameters module 414 uses the neural state assessment made by module 412, as well as other feedback inputs described in more detail below, to determine the appropriate stimulation parameters to address the assessed neural state.

For example, where the neural stimulation is electrical signals, the stimulation parameters may be frequency, pulse duration, duty cycle, etcetera. Module 414 then provides the stimulation parameters to neural stimulator module 416, which in turn provides neural stimulations according to the selected stimulation parameters to brain 404. Neural stimulator module 416 may be implemented as a DBS stimulator. Neural activity is recorded in order to allow a subsequent assessment of the impact of neural stimulations applied by neural stimulator module 416. Recorded neural activity is fed back to analyzer module 406 and neural stimulator module 414 to further inform the subsequent features extractions made by analyzer module 406 and the subsequent selection of neural stimulation parameters made by module 414.

Thus, neural stimulation system 400, and specifically the combined effects of analyzer module 406, muscle contractions or movements module 408, other inputs module 410 and neural state assessment module 412, significantly expand the scope of data that may be used to both assess current and future neural states, and to inform the selection of neural stimulation parameters made by module 414. Significantly, the additional data accessed by neural stimulation system 400 are derived from muscle contractions or movements, which are non-invasive and generally safer and less costly to gather than direct neural readings made by, for example, electrodes inserted within brain 404. Neural stimulation system 400 additionally provides access to an even wider range of historical data of human 402 that may be provided to analyzer module 406 for feature extraction analysis. For example, cloud 50 may provide information on from social graphs, emails, recorded interviews and conversations of human 402.

Figures 5, 6:
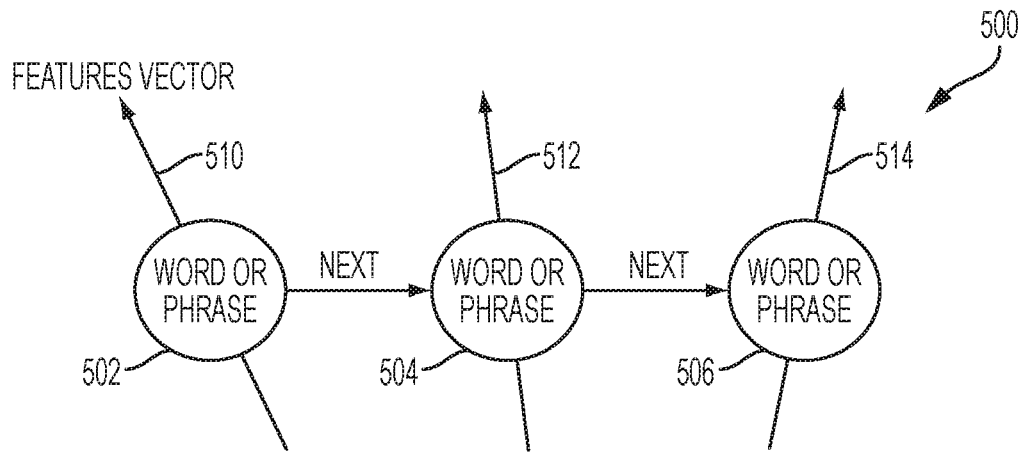
FIG. 5 depicts a graphical text analyzer's output feature vector comprising an ordered set of words or phrases, wherein each is represented by its own vector according to one or more embodiments.
FIG. 6 depicts various equations illustrating a core algorithm of a graphical text analyzer in accordance with one or more embodiments.

A more specific implementation of neural stimulation system 400 will now be described with reference to FIGS. 5-8, wherein the detected muscle contractions or movements of human 402 (shown in FIG. 4) are speech, the detected speech is converted to text, the feature extraction is performed by a graphical text analyzer, and the neural stimulator is a DBS stimulator. Referring now to FIG. 5, there is depicted a graphical text analyzer's output feature vector in the form of a word graph 500 having an ordered set of words or phrases shown as nodes 502, 504, 506, each represented by its own features vector 510, 512, 514 according to one or more embodiments. Each features vector 510, 512, 514 is representative of some additional feature of its corresponding node 502, 504, 506 in some word/feature space. Word graph 500 is useful to extract topological features for certain vectors, for example, all vectors that point in the upper quadrant of the feature space of words. The dimensions of the word/feature space might be parts of speech (verbs, nouns, adjectives), or the dimensions may be locations in a lexicon or an online resource of the semantic categorization of words in a feature space such as WordNet, which is the trade name of a large lexical database of English. In WordNet, nouns, verbs, adjectives and adverbs are grouped into sets of cognitive synonyms (synsets), each expressing a distinct concept. Synsets are interlinked by means of conceptual-semantic and lexical relations. The resulting network of meaningfully related words and concepts can be navigated with a browser. WordNet is also freely and publicly available for download from the WorldNet website, www.worldnet.princeton.edu. The structure of WordNet makes it a useful tool for computational linguistics and natural language processing.

FIG. 6 depicts Equations A-H, which illustrate features of a core algorithm that may be implemented by an analyzer module 406A (shown in FIG. 7) having a graphical text analysis module 702 (shown in FIG. 7) according to one or more embodiments. Analyzer module 406A is an implementation of analyzer module 406 (shown in FIG. 4), wherein muscle contractions or movements of human 402 in the form of speech is detected by module 408 (shown in FIG. 4) and converted to text by other inputs module 410.

Figure 7:
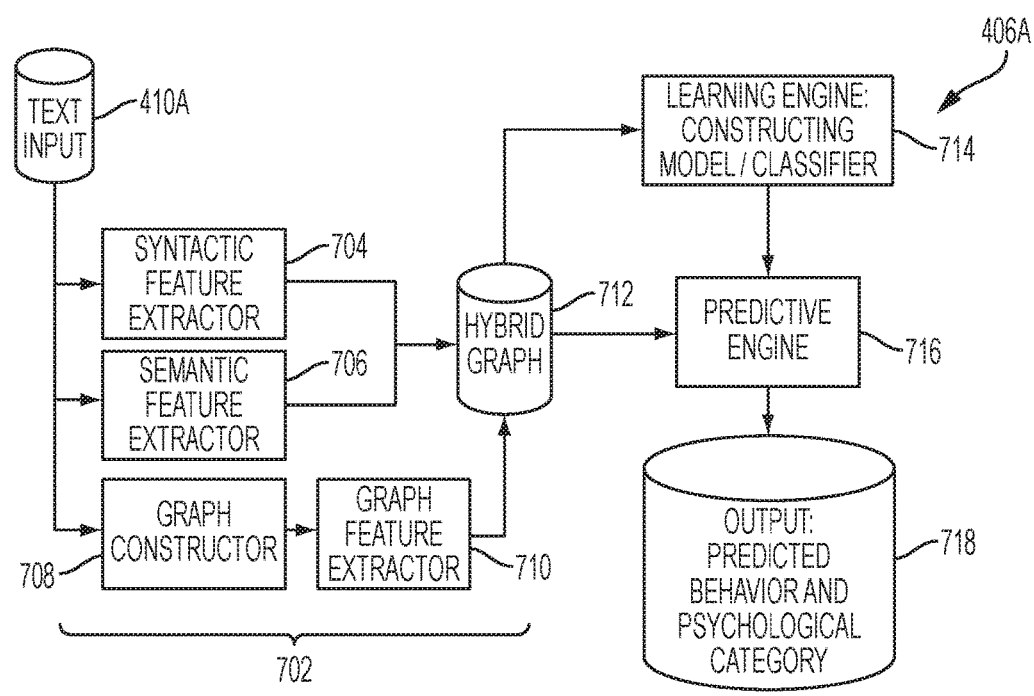
FIG. 7 depicts of a diagram of a graphical text analysis and brain stimulation system according to one or more embodiments.

Continuing with a description of Equations A-H of FIG. 6 including selected references to corresponding elements of analyzer module 406A and graphical text analysis module 702 shown in FIG. 7, text or speech-to-text is fed into a standard lexical parser (e.g., syntactic feature extractor 704 of FIG. 7) that extracts syntactic features, which are converted to vectors. Such vectors can have binary components for the syntactic categories verb, noun, pronoun, etcetera, such that the vector represented by Equation A represents a noun word.

The text is also fed into a semantic analyzer (e.g., semantic feature extractor 706 of FIG. 7) that converts words into semantic vectors. The conversion into semantic vectors can be implemented in a number of ways, including, for example, the use of latent semantic analysis. The semantic content of each word is represented by a vector whose components are determined by the singular value decomposition of word co-occurrence frequencies over a large database of documents. As a result, the semantic similarity between two words "a" and "b" can be estimated by the scalar product of their respective semantic vectors represented by Equation B.

A hybrid graph is created in accordance with Equation C in which the nodes "N" represent words or phrases, the edges "E" represent temporal precedence in the speech, and each node possesses a feature vector "W" defined as a direct sum of the syntactic and semantic vectors plus additional non-textual features (e.g. the identity of the speaker) as given by Equation D.

The graph "G" of Equation C is then analyzed based on a variety of features, including standard graph-theoretical topological measures of the graph skeleton as shown by Equation E, such as degree distribution, density of small-size motifs, clustering, centrality, etcetera. Similarly, additional values can be extracted by including the feature vectors attached to each node. One such instance is the magnetization of the generalized Potts model as shown by Equation F such that temporal proximity and feature similarity are taken into account.

The features that incorporate the syntactic, semantic and dynamical components of speech are then combined as a multi-dimensional features vector "F" that represents the speech sample. This feature vector is finally used to train a standard classifier according to Equation G to discriminate speech samples that belong to different conditions "C," such that for each test speech sample the classifier estimates its condition identity based on the extracted features represented by Equation H.

FIG. 7 depicts a diagram of an analyzer module 406A having a graphical text analysis module 702 according to one or more embodiments. Analyzer module 406A is an implementation of analyzer module 406 (shown in FIG. 4), and text input 410A is an implementation of other inputs module 410 (shown in FIG. 4). Analyzer module 406A includes text input 410A, a syntactic feature extractor 704, a semantic feature extractor 706, a graph constructor 708, a graph feature extractor 710, a hybrid graph module 712, a learning engine 714, a predictive engine 716 and an output module 718, configured and arranged as shown. In general, graphical text analyzer 702 functions to convert inputs from text input module 410A into hybrid graphs (e.g., word graph 500 shown in FIG. 5), which is provided to learning engine 714 and predictive engine 716. In addition to the graphical text analyzer algorithm illustrated in FIG. 6 and described above, additional details of the operation of graphical text analyzer 702 are available in a publication entitled Speech Graphs Provide A Quantitative Measure Of Thought Disorder In Psychosis, authored by Mota et al., and published by PLOS ONE, April 2012, Volume 7, Issue 4, the entire disclosure of which is incorporated by reference herein in its entirety.

As noted, graphical text analyzer 702 provides word graph inputs to learning engine 714, and predictive engine 716, which constructs predictive features or model classifiers of the state of the individual in order to predict what the next state will be, i.e., the predicted behavioral or psychological category of output module 718. Accordingly, predictive engine 716 and output module 718 may be modeled as Markov chains. The Markovian model output from output module 718 may be fed into neural stimulation parameter module 414 (shown in FIG. 4) to parameterize neural stimulation module 416 (shown in FIG. 4), which may be implemented as a DBS. Accordingly, when a particular undesired psychological state is predicted by analyzer 406A, the undesired psychological state may be averted through the parameterization of neural stimulation module 416. The actual neural activity may be recorded (e.g., recorded neural actively shown in FIG. 4) and fed back into predictive engine 716 to predict the next state that will be given to neural stimulation parameters module 414 to parameterize neural stimulator module 416.

Figure 8:
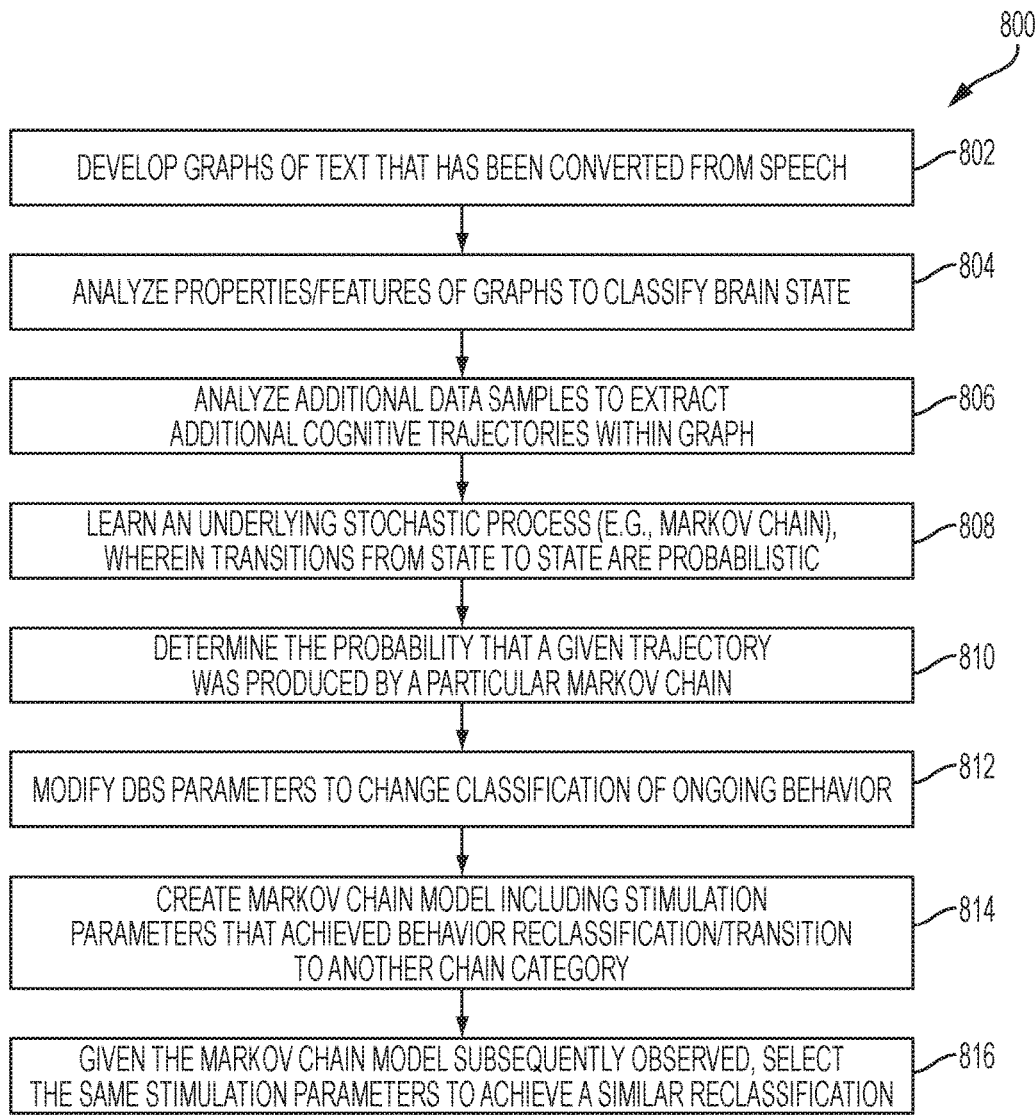
FIG. 8 depicts a flow diagram of a methodology according to one or more embodiments.

FIG. 8 depicts a flow diagram of a methodology 800 performed by analyzer 406A (shown in FIG. 7) according to one or more embodiments. Methodology 800 begins at block 802 by developing graphs of text that has been converted from speech. At block 804, properties/features of graphs are analyzed to classify or assign human 402 (shown in FIG. 4) in a particular time window of speech to a particular brain state. The classification or assignment may be based on a scale, such as the Positive and Negative Syndrome Scale (PANSS), which is a medical scale used for measuring symptom severity of patients with schizophrenia. Note that PANSS scale ratings are performed according to a known specific protocol. However, the classification or assignment made at 804 is a prediction of a PANSS scale rating, based on a configuration and training of the system to make this prediction, for example, by having trained the system on labelled data from patients. With human 402 classified into a particular brain state (e.g., a predicted PANSS scale rating), block 806 analyzes additional data samples to extract additional cognitive trajectories within the graph. The additional data samples may include written text, EEG measurements, deep brain electrophysiology, behaviors in the world, etcetera, derived from cloud 50 (shown in FIGS. 3 and 4), wearable devices (not shown) on human 402, implanted DBS electrodes, and others.

At block 808, an underlying stochastic process (e.g., a Markov chain) is analyzed, wherein transitions from state to state are probabilistic. In other words, the transitions from state to state are governed by probability such that the behavior of the probabilistic system cannot be predicted exactly but the probability of certain behaviors is known. At block 810, the probability that a given trajectory was produced by a particular Markov chain is determined. Continuing with the example wherein the determination of the brain state is based on a predicted PANSS scale, by observing predicted PANSS scales over time as well as the correlated speech features, a Markov-based model of cognitive states and how those states are changing may be derived. For example, human 402 may have two ways of having a schizophrenic episode. The predicted PANSS scale might change very rapidly, or it might change very gradually. Thus, the disclosed Markov model conveys whether or not human 402 is in a brain state that is about to change rapidly or gradually, which allows methodology 800 at block 812 to modify DBS parameters to change the classification of ongoing behavior. At block 814 a Markov chain model is created including stimulation parameters that achieved behavior reclassification/transition to another chain category. At block 816, given the Markov chain model subsequently observed, the same stimulation parameters are selected to achieve a similar reclassification.

Thus, block 810 allows block 812 to make a prediction about the DBS parameters that may be required to avert the brain state change identified by the predicted PANSS scale. The selected DBS parameters depend on whether the Markov state is changing rapidly or gradually. The selected parameters may then be validated by ongoing recordings of speech from human 402 with subsequent iterations of methodology 800 mapping the features of human 402's speech and other additional data back to the predicted PANSS scale in order to determine whether or not the Markov model needs to be updated, and also to determine whether or not whether the selected DBS parameter change has been effective. New Markov states are continuously constructed until, over time, Markov states have been constructed for every state that may be a target for stimulation. This creates a Markov scale that can be used to identify multiple additional states. For example, it may be identified that a predicted PANSS scale is about to change rapidly, that a predicted PANSS scale is about to change gradually, that a predicted PANSS scale is about to change rapidly and a DBS stimulation has been provided with certain parameters, or that a predicted PANSS scale is about to change gradually and a DBS stimulation has been provided with certain other parameters. This allows DBS stimulation parameters to be selected in real time, and to be informed by information that is broader in scope and safer and less costly to acquire than just the recorded brain activity (as shown in FIG. 4) acting alone.

Thus it can be seen from the forgoing detailed description that one or more embodiments of the present disclosure provide technical benefits and advantages. The disclosed neural stimulation system non-invasively analyzes data derived from either voluntary or involuntary muscle contractions or movements (e.g., speech, EEG measurements, pulse, heart rate, text converted from speech, video etc.) to construct features, then correlate those features with neural states to parameterize a neural stimulation (e.g., a DBS). The detected indicators of a particular cognitive state or a disease state can be prescriptive of the therapeutic parameter of the neural stimulation, as well as provide an indication of whether or not the applied neural stimulation has moved the neural state toward restoration of a normal, health state.

More specifically, the disclosed neural stimulation system combines machine learning, graph theoretic and natural language techniques to implement real-time analysis of behavior, including speech, to provide quantifiable features extracted from in-person interviews, teleconferencing or offline sources (email, phone) for categorization of psychological states. The disclosed system collects both real time and offline behavioral streams such as speech-to-text and text, video and physiological measures such as heart rate, blood pressure and galvanic skin conductance. In some embodiments, speech and text data are analyzed online for a multiplicity of features, such as semantic content and syntactic structure in the transcribed text, emotional value from the audio, and video and physiological streams. The analyzed speech and text are then combined with offline analysis of similar streams produced by the patient and by the population. The disclosed methods of extracting semantic vectors (e.g., latent semantic analysis and WordNet) allow the computation of a distance between words and specific concepts (e.g., introspection, anxiety, depression), such that the text can be transformed into a field of distances to a concept, a field of fields of distances to the entire lexicon, or a field of distances to other texts including books, essays, chapters and textbooks.

The syntactic and semantic features are combined either as an assemblage of features or as integrated fields, such as the Potts model. Similarly, locally embedded graphs may be constructed such that a trajectory in a high-dimensional feature space is computed for each text. The trajectory is used as a measure of coherence of the speech, as well as a measure of distance between speech trajectories using methods such as dynamic time warping. The extracted multi-dimensional features are then used as predictors for psychological states (such as communication and cognitive style, or psychiatric disorders) based on training with pre-labeled interviews with test individuals. This method produces models that transform text into a field of numerical values that indicate the probability that a subject belongs to a particular psychological or psychiatric category, or that the particular subject will likely enter a particular psychological or psychiatric category in the near future. The disclosed neural stimulation system and methodology are flexible in that other data modalities can be similarly analyzed and correlated with text features and categorization to extend the analysis beyond speech.

Figure 9:
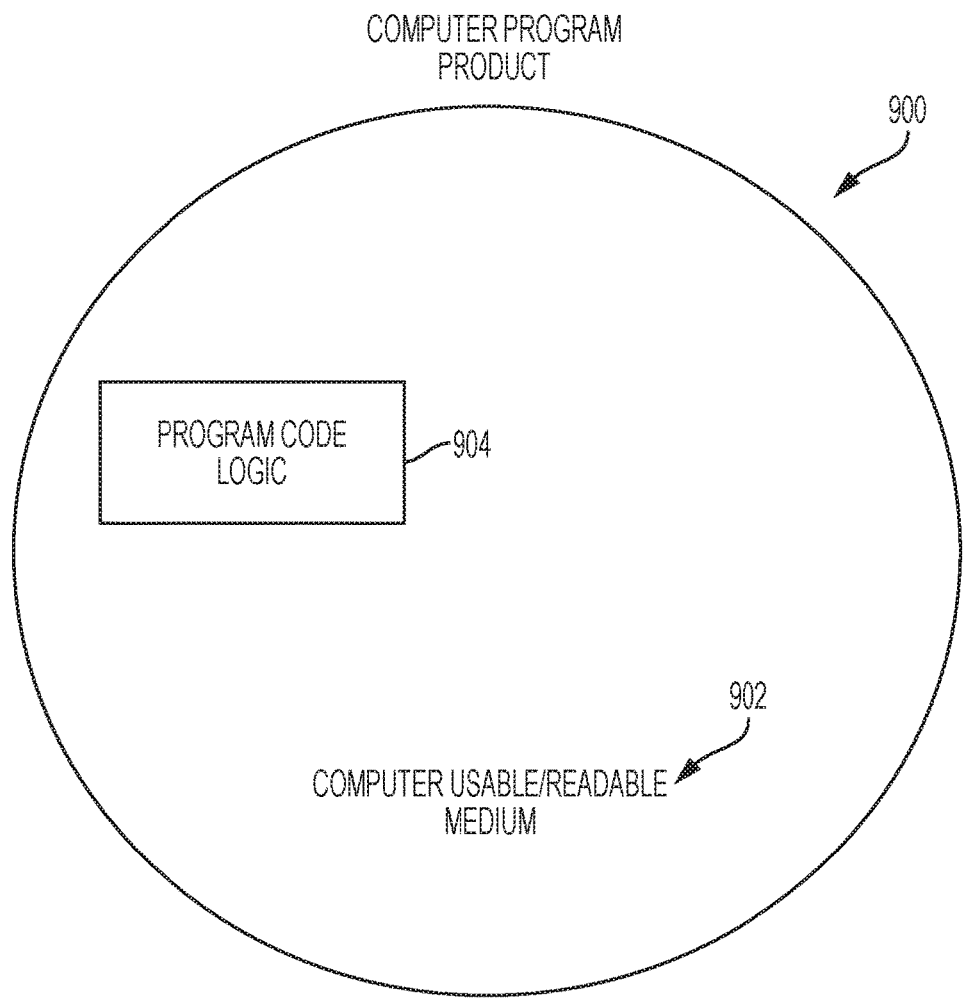
FIG. 9 depicts a diagram of a computer program product according to one or more embodiments.

Referring now to FIG. 9, a computer program product 900 in accordance with an embodiment that includes a computer readable storage medium 902 and program instructions 904 is generally shown.

The present disclosure may be a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the present disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

What is claimed is:

1. A neural stimulation system having a non-transitory computer readable medium having program instructions readable by a processor circuit of the neural stimulation system for implementing the neural stimulation system, the processor circuit of the neural stimulation system comprising:
   a first module configured to derive neural data from muscle contractions or movements of a subject;

a graphical text analysis module communicatively coupled to the first module and configured to derive neural state assessment data that represents a neural state assessment of the subject based at least in part on the neural data; and a third module communicatively coupled to the graphical text analysis module and a fourth module;

wherein the fourth module is configured to deliver electrical neural stimulation through an electrode to a selected location of the subject;

wherein the third module is configured to derive, based at least in part on the neural state assessment data, at least one neural stimulation parameter of the electrical neural stimulation delivered through the electrode to the selected location of the subject;

wherein the graphical text analysis module is further configured to convert the neural data to a graphical set of vectors.

2. The system of claim 1, wherein at least one of the first module, the graphical text analysis module, the third module and the fourth module comprises a node of a cloud.

3. The system of claim 1, wherein:
the first module comprises an other inputs module and a muscle contractions or movements module;
the graphical text analysis module comprises an analyzer module and a neural state assessment module;
the third module comprises a neural stimulation parameter module; and
the fourth module comprises a neural stimulator.

4. The system of claim 1, wherein:
the neural data is derived from text;
the muscle contractions or movements produce speech; and
the first module is further configured to convert speech to text.

5. The system of claim 1, wherein the vectors categorize a neural state of the subject.

6. The system of claim 5, wherein the graphical text analysis module is further configured to:
provide a first category of a cognitive state of the subject; and
use the first category to predict a cognitive trajectory and to update the at least one neural stimulation parameter.

7. The system of claim 6, wherein:
the first module is further configured to derive additional neural data samples; and
the additional neural data samples provide predictions of additional cognitive trajectories within the graphical set of vectors.

8. The system of claim 7, wherein the additional neural data samples are derived from at least one of:
a written text;
an electroencephalogram (EEG);
a deep brain electrophysiology; and
at least one behavior of the subject.

9. The system of claim 8 wherein:
the graphical text analysis module is further configured to calculate a probability that any of the cognitive trajectory and the additional cognitive trajectories was produced by a particular Markov chain.

10. The system of claim 8, wherein:
the additional data samples comprise the at least one neural stimulation parameter; and
a second classification of cognitive state comprises a determination that a change in the neural state of the subject was beneficial.

11. The system of claim 10, wherein the third module is further configured to select the at least one neural stimulation parameter based on an assessment that the at least one neural stimulation parameter has achieved a reclassification of the neural state of the subject.

12. A computer program product for implementing a neural stimulation system, the computer program product comprising:
a computer readable storage medium having program instructions embodied therewith, wherein the computer readable storage medium is not a transitory signal per se, the program instructions readable by a processor circuit to cause the processor circuit to perform a method comprising:
deriving, by the processor, neural data from muscle contractions or movements of a subject;
deriving, by the processor, neural state assessment data that represents a neural state assessment of the subject based at least in part on the neural data;
controlling an electrode to deliver electrical neural stimulation through the electrode to a selected location of the subject; and
using graphical text analysis to derive, by the processor, based at least in part on the neural state assessment data, at least one neural stimulation parameter of the electrical neural stimulation delivered through the electrode to the selected location of the subject;
wherein deriving the neural state assessment data that represents a neural state assessment of the subject based at least in part on the neural data comprises converting the neural data to a graphical set of vectors.

13. The computer program product of claim 12, wherein:
the neural data is derived from text;
the muscle contractions or movements produce speech; and
the deriving neural data from muscle contractions or movements comprises converting speech to text.

14. The computer program product of claim 13, wherein the vectors categorize a neural state of the subject.

15. A computer implemented neural stimulation system, the system comprising:
a first module configured to derive neural data from muscle contractions or movements of a subject;
a second module communicatively coupled to the first module and configured to derive neural state assessment data that represents a neural state assessment of the subject based at least in part on the neural data; and
a third module communicatively coupled to the second module and a fourth module;
wherein the fourth module is configured to deliver electrical neural stimulation through an electrode to a selected location of the subject;
wherein the third module is configured to derive at least one neural stimulation parameter of the electrical neural stimulation based at least in part on the neural state assessment data;
wherein the second module is further configured to convert the neural data to a graphical set of vectors.

16. The system of claim 15, wherein at least one of the first module, the second module, the third module and the fourth module comprises a node of a cloud.

17. The system of claim 15, wherein the vectors categorize a neural state of the subject.

* * * * *